US011369290B2

(12) United States Patent
Ikeuchi

(10) Patent No.: US 11,369,290 B2
(45) Date of Patent: Jun. 28, 2022

(54) ASSIST DEVICE CONTROL SYSTEM

(71) Applicant: Honda Motor Co., Ltd., Tokyo (JP)

(72) Inventor: Yasushi Ikeuchi, Saitama (JP)

(73) Assignee: Honda Motor Co., Ltd., Tokyo (JP)

( * ) Notice: Subject to any disclaimer, the term of this patent is extended or adjusted under 35 U.S.C. 154(b) by 370 days.

(21) Appl. No.: 16/810,867

(22) Filed: Mar. 6, 2020

(65) Prior Publication Data

US 2020/0289030 A1 Sep. 17, 2020

(30) Foreign Application Priority Data

Mar. 11, 2019 (JP) .............................. JP2019-043742

(51) Int. Cl.
*A61B 5/11* (2006.01)
*B25J 9/00* (2006.01)
*A61F 5/02* (2006.01)
*A61H 3/00* (2006.01)

(52) U.S. Cl.
CPC ............. *A61B 5/112* (2013.01); *A61B 5/1116* (2013.01); *A61F 5/024* (2013.01); *A61F 5/028* (2013.01); *A61H 3/00* (2013.01); *B25J 9/0006* (2013.01)

(58) Field of Classification Search
CPC ........ A61B 5/112; A61B 5/1116; A61F 5/024; A61F 5/028; A61H 3/00; B25J 9/0006
See application file for complete search history.

(56) References Cited

U.S. PATENT DOCUMENTS

2009/0024061 A1  1/2009  Ueda et al.
2018/0140496 A1  5/2018  Sankai et al.

FOREIGN PATENT DOCUMENTS

| CN | 106618965 | 5/2017 |
| CN | 106621209 | 5/2017 |
| CN | 108345269 | 7/2018 |
| WO | 2014148038 | 9/2014 |
| WO | 2016038824 | 3/2016 |
| WO | 2016180074 | 11/2016 |

OTHER PUBLICATIONS

"Office Action of China Counterpart Application" with English translation thereof, dated Nov. 26, 2021, p. 1-p. 11.

*Primary Examiner* — Curtis B Odom
(74) *Attorney, Agent, or Firm* — JCIPRNET

(57) ABSTRACT

An assist device control system is provided. The control system includes an improvement effect data storing unit that stores improvement effect data, which represents a correlation between an improvement effect and an assist force, for each target item for every reference unit period for a plurality of types of target items, a data recognizing unit that recognizes the improvement effect data for each of a plurality of target items, and a schedule determining unit that compares the recognized improvement effect data, determines a target item to be prioritized for every reference unit period, and determines the assist force to be generated for every reference unit period on the basis of the improvement effect data of the target item to be prioritized.

8 Claims, 9 Drawing Sheets

ASSIST DEVICE CONTROL SYSTEM

CROSS-REFERENCE TO RELATED APPLICATION

This application claims the priority of Japan patent application serial no. 2019-043742, filed on Mar. 11, 2019. The entirety of the above-mentioned patent application is hereby incorporated by reference herein and made a part of this specification.

BACKGROUND

Technical Field

The disclosure relates to an assist device control system controlling an assist device that generates an assist force corresponding to a user's operation.

Description of Related Art

Conventionally, assist devices generating an assist force used for assisting with drive of a user's joints in the user's legs or the like in order to assist the user with operations such as walking, bending, stretching, and the like are known. In addition, assist device control systems controlling the magnitude, the generation timing, and the like of an assist force generated by an assist device are known (for example, see Patent Document 1).

In the assist device control system disclosed in Patent Document 1, data representing correlations between constitutions and gaits of a plurality of users is collated through assist devices used by the plurality of users. Then, this assist device control system determines an assist force to be generated when applied to a user who is a target of the assist on the basis of the data and controls drive of an assist device that is a target of the control on the basis of the assist force.

Patent Documents

[Patent Document 1] PCT Publication No. 2016/038824

However, for example, in a case in which an assist device is used for training or rehabilitation, there are cases in which a physical function to be enhanced with priority differs in accordance with a time period during a period in which the training or the rehabilitation is performed.

For example, in a case in which the purpose is rehabilitation, there are also cases in which enhancing balance between left and right muscle strength quantities is prioritized in an initial step, and extending an operation holding period is prioritized in subsequent steps after the initial step. In a case in which physical functions to be enhanced with priority differ, assist forces to be generated by the assist device also differ.

However, the assist device control system disclosed in Patent Document 1 is only for the purpose of assisting a user with walking on the basis of the data representing the correlations between constitutions and gaits of users but does not change an assist force to be generated for each time period. For this reason, even when an assist force is generated on the basis of control according to this system, it is difficult to obtain sufficient effects in the entire assist period depending on the purpose of the use and the like of the assist device.

SUMMARY

An assist device control system according to an embodiment is an assist device control system controlling an assist device that generates an assist force corresponding to an operation of a user during a predetermined assist period, the assist device control system including: an improvement effect data storing unit that stores improvement effect data, which represents a correlation between an improvement effect that is an effect on the user according to the assist force and the assist force, for each target item for every reference unit period set by delimiting the assist period for a plurality of types of target items; a data recognizing unit that recognizes a plurality of the target items and recognizes the improvement effect data for each of the target items; and a schedule determining unit that compares the improvement effect data being recognized, determines a target item to be prioritized from among the target items being recognized for every reference unit period, and determines the assist force to be generated for every reference unit period on the basis of the improvement effect data corresponding to the determined target item to be prioritized.

DESCRIPTION OF THE EMBODIMENTS

Figure 1:
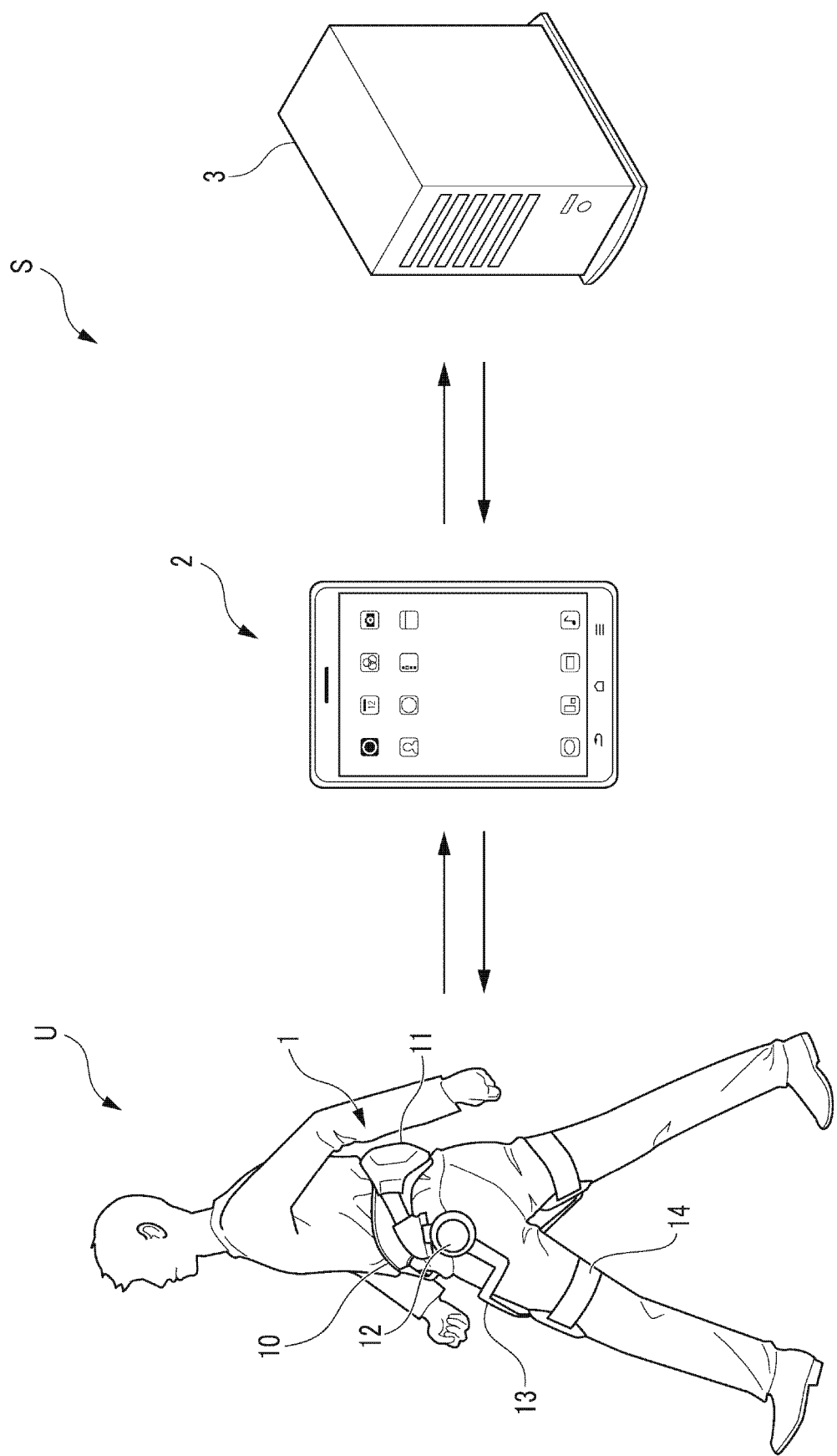
FIG. 1 is a schematic view illustrating the configuration of a control system according to an embodiment.

The embodiments of the disclosure provide an assist device control system capable of generating an efficient assist force in the entire assist period.

Here, "improvement effect data" more specifically represents data representing a correlation between an improvement effect that is a degree of improvement of a target item and details of assist forces (in other words, assist forces to be generated) applied to the user. For example, the improvement effect data is data representing a correlation between a height of the improvement rate of a user's current athletic capability or a degree of a user's physical load or a psychological load and magnitudes of torques of assist forces to be applied or the like.

In this way, the assist device control system according to one or some exemplary embodiments of the disclosure recognizes a plurality of target items and improvement effect data for such target items. Then, this control system compares improvement effect data relating to a plurality of types of the target items being recognized and determines a target item to be prioritized and an assist force to be generated for improving the target item for every reference unit period.

In this way, an assist force having a high improvement effect is determined as an assist force to be generated for every reference unit period set by delimiting the assist period. Therefore, according to the assist device control system of one or some exemplary embodiments of the disclosure, an assist force that is effective in the entire assist period can be generated.

For example, according to this assist device control system, an assist force having high efficiency for training or rehabilitation or an assist force having a low physical load or a low psychological load for a user in the entire assist period can be generated.

In addition, in the assist device control system according to the embodiment, for example, a secondary effect data storing unit that stores secondary effect data, which represents a correlation between a secondary effect that is an effect different from the improvement effect applied to the user in accordance with the assist force and the assist force for each secondary item that is an item different from the target items, for a plurality of types of secondary items for every reference unit period is further included, and the data recognizing unit recognizes the plurality of target items and recognizes at least one of the secondary items, recognizes the improvement effect data for each of the target items being recognized and the secondary effect data for the secondary items being recognized, and recognizes ratio data that is a ratio between a degree of the improvement effect and a degree of the secondary effect on the basis of each piece of the improvement effect data and the secondary effect data that have been recognized, and the schedule determining unit compares the ratio data being recognized and determines a target item to be prioritized from among the target items being recognized for every reference unit period.

Here, "secondary items" more specifically represents items that are different from target items and are not set for the original purpose by the user or the like. The secondary items include not only positive items such as muscle strength of another portion improved together with muscle strength of a target portion of rehabilitation but also negative items such as fatigue occurring in accordance with the rehabilitation and a decrease in motivation for the rehabilitation.

In addition, here, "secondary effect data" more specifically represents data representing a correlation between a secondary effect and details of assist forces (in other words, assist forces to be generated) applied to the user.

An improvement effect in the entire assist period may consequently decrease when an assist force having a high improvement effect and a high secondary effect is generated. Thus, in this way, when assist forces to be generated are determined by referring to ratio data that is a ratio between a secondary effect and an improvement effect, an assist force that is more efficient in the entire assist period can be generated.

In addition, in the assist device control system according to the embodiment, for example, the data recognizing unit recognizes the target items on the basis of attributes of the user.

Here, "attributes of a user" include not only attributes of the user but also attributes relating to an event relating to the user. For example, in addition to a user's characteristic and a user's request (a behavior (for example, walking, conversation, or the like) that the user desires to perform as a result of training or rehabilitation), the purpose of the training, a medical condition that is the cause of the rehabilitation, a time period thereof, and the like are included in the attributes of the user.

In this way, when target items and improvement effect data for the target items are recognized in accordance with the attributes of the user, an assist force determined to be generated in accordance therewith can efficiently enhance items that are appropriate for the user's requests and situations.

In addition, in the assist device control system according to the embodiment, the schedule determining unit compares the improvement effect data being recognized and determines a generation unit period by adjusting each reference unit period, determines the target item to be prioritized from among the target items recognized for every generation unit period, and determines the assist force to be generated for every generation unit period on the basis of the improvement effect data corresponding to the determined target item to be prioritized.

For example, in a case in which the assist device is used for rehabilitation, training, or the like, a date may be employed as a reference unit period. However, when focusing only on the improvement effect of an assist force, there are also cases in which an assist force regarded to be effective is different in a first half and a second half of a time during which rehabilitation or training is performed even on the same day.

In other words, when a timing for performing switching between assist forces to be generated is determined by focusing only on the reference unit period, an assist force that may not be regarded to be effective may be generated in a part of the reference unit period.

Thus, in this way, when a schedule for generating assist forces is determined, by determining a generation unit period by adjusting the reference unit period and determining an assist force to be generated for every generation unit period, timings at which switching between assist forces to be generated is performed can be formed more appropriate.

Hereinafter, a control system S (an assist device control system) according to an embodiment will be described with reference to the drawings. In this embodiment, a case in which rehabilitation relating to walking of a user U is performed during a predetermined rehabilitation period (assist period) using an assist device 1 controlled by the control system S will be described.

However, the assist device control system according to one or some exemplary embodiments of the disclosure may generate an assist force corresponding to a user's operation but is not limited to a control system for a walking assist device used for rehabilitation.

For example, the assist device control system may be used not for rehabilitation but for training. In addition, for example, the assist device described above may be an assist device which is used for assisting with an operation of lifting an object by applying an assist force to a user's arm or waist during a period in which the operation is performed, and the assist device control system described above may be an assist device control system used for controlling such an assist device.

First, a schematic configuration of the control system S will be described with reference to FIGS. 1 to 3.

As illustrated in FIG. 1, the control system S includes an assist device 1, which is a so-called walking assist device, worn by a user U and assisting the user U with walking, a tablet 2 that is an information terminal controlling an assist force to be generated and applied from the assist device 1 to the user, and a server 3 that performs a process of determining the assist force to be generated.

The assist device 1 and the tablet 2 are configured to be able to perform information communication with each other through wired communication such as a communication cable or radio communication such as near field communication. The tablet 2 and the server 3 are configured to be able to perform information communication with each other through an Internet line or the like.

Figure 2:
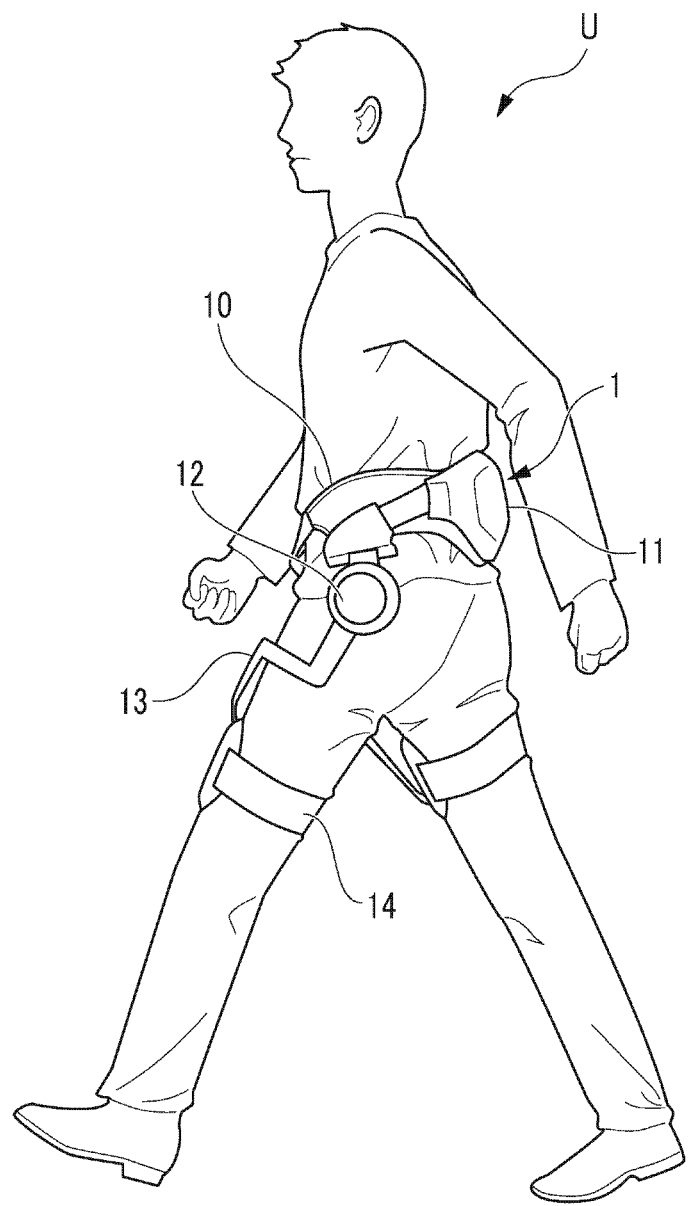
FIG. 2 is a side view illustrating the configuration of an assist device controlled by the control system illustrated in FIG. 1.

As illustrated in FIG. 2, the assist device 1 includes a waist brace 10 that is worn on the waist of the user U, a main part 11 that is fixed to cover both side faces from a rear face of the waist of the user U through the waist brace 10, one pair of left and right actuators 12 that are mounted on left and right side faces of the main part 11, one pair of left and right frame parts 13 that are installed to extend downward from the actuators 12, and one pair of left and right thigh orthoses 14 that are mounted at ends of the lower sides of the frame part 13 and are fixed to the thighs of the user U.

The actuators 12 are positioned on lateral sides of the thighs or lateral sides of the waist of the user U in a state in which the user U wears the assist device 1. The frame parts 13 and the thigh orthoses 14 mounted on the frame parts 13 can freely oscillate forward and backward with respect to the actuators 12.

In the assist device 1 configured in this way, drive forces from the actuators 12 are delivered to the thighs of the user U through the frame parts 13 and the thigh orthoses 14. Accordingly, assistance forces causing the thighs to oscillate forward and backward for assisting the user U with walking are given to the thighs of the user U.

The main part 11 includes a communication unit (not illustrated in the drawing) used for performing information communication with the tablet 2. The assist device 1 controls assist forces to be generated in accordance with an instruction transmitted from the tablet 2 through the communication unit.

More specifically, the assist device 1 controls magnitudes of drive forces (torques) to be output, output timings of torques (torque patterns), balance between left and right torques (a ratio between lengths of times in which legs are lifted), a phase difference between left and right torques that are periodically generated, and the like by controlling outputs of the actuators 12 in accordance with the instruction.

The tablet 2 is an information terminal used for performing presentation of information transmitted from the assist device 1, input of information required for determining assist forces to be generated, presentation of assist forces, which will be generated, determined by the server 3 (more specifically, an entire schedule to be described later), and setting of assist forces to be generated.

In this embodiment, the assist device 1 is used for the purposes of training and rehabilitation. For this reason, input of information, setting of assist forces, and the like are performed on the tablet 2 also by a physical therapist (hereinafter referred to as "PT") and the like supervising rehabilitation of the user U in addition to the user U.

An information terminal that can be used for the assist device control system according to one or some exemplary embodiments of the disclosure is not limited to a tablet as in this embodiment but may be any device that can perform inputting of information from a user or the like, setting command for the assist device. For example, the information terminal may be a laptop computer, a smartphone, or the like.

Figure 3:
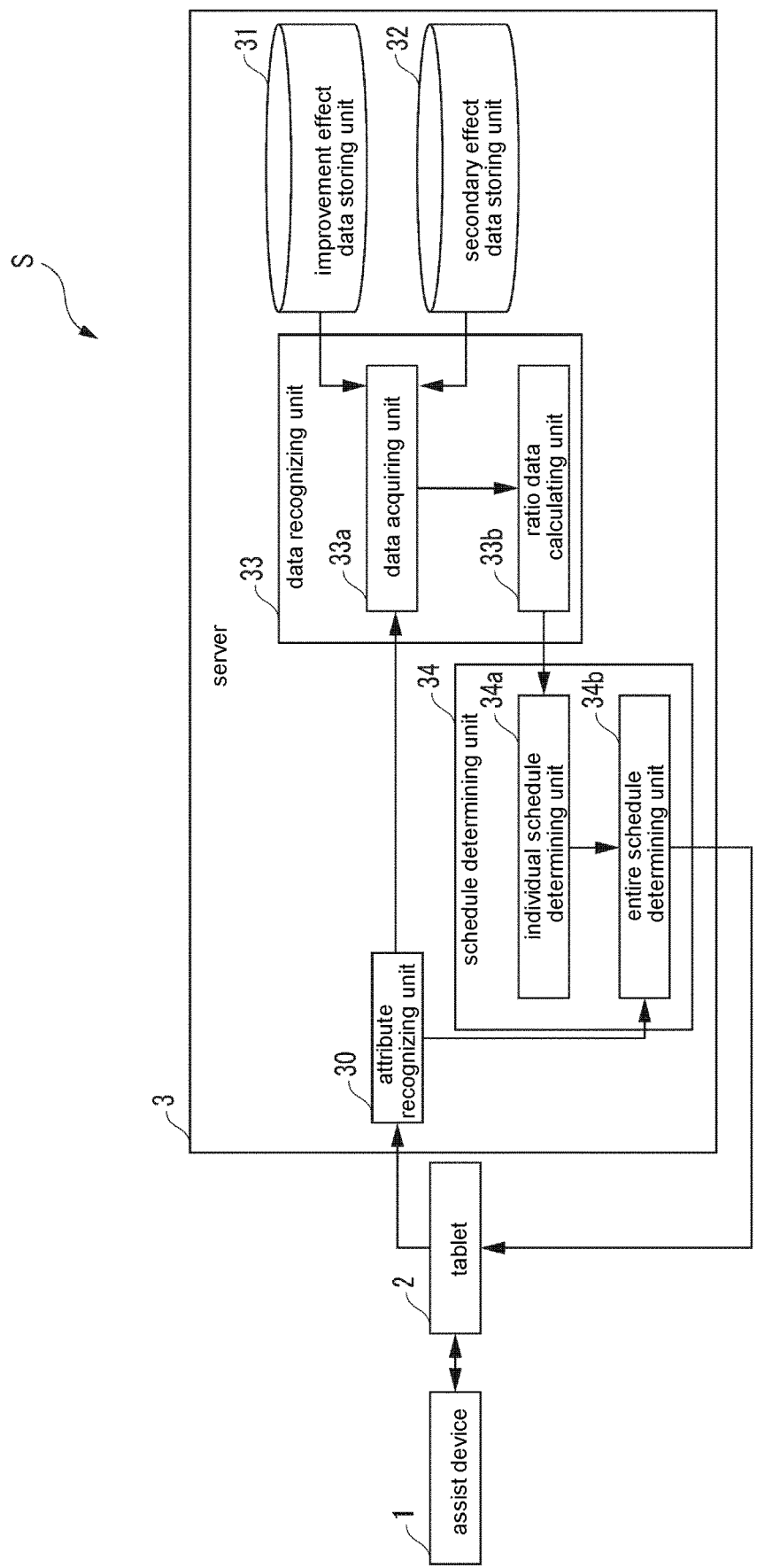
FIG. 3 is a block diagram illustrating the system configuration of the control system illustrated in FIG. 1.

As illustrated in FIG. 3, the server 3 includes an attribute recognizing unit 30 that recognizes attributes of a user U, an improvement effect data storing unit 31 that stores improvement effect data, a secondary effect data storing unit 32 that stores secondary effect data, a data recognizing unit 33 that recognizes the improvement effect data and the secondary effect data, and a schedule determining unit 34 that determines a schedule for assist forces to be generated for the user U as mounted hardware components or functions (processing units) realized by a program.

The attribute recognizing unit 30 recognizes attributes of the user U input to the tablet 2. An input to the tablet 2 is performed by the user U and is also performed by a PT supervising the rehabilitation of the user and the like.

Here, attributes relating to an event relating to the user U are included in addition to attributes of the user U in the attributes of the user. For example, in addition to a user's characteristic and a user's request (a behavior (for example, walking, conversation, or the like) that the user desires to perform as a result of rehabilitation), a medical condition that is the cause of the rehabilitation, a time period thereof, and the like are included in the attributes of the user U.

In this embodiment, the attributes of the user U are recognized on the basis of information input to the tablet 2 by the user U or the like. However, the assist device control system according to one or some exemplary embodiments of the disclosure is not limited to such a configuration. For example, in a case in which the system does not include a tablet or the like, the server may directly recognize attributes of the user from a database that is separately prepared rather than through the input of the user or the like.

The improvement effect data storing unit 31 stores improvement effect data for every reference unit period set by delimiting an assist period for a plurality of types of target items.

Here, a "target item" is an item corresponding to an effect on the user U as a result of an operation with which the assist device assists and represents an item that is a target of which improvement or the like is to be achieved by the user U. The target items are set in advance in accordance with the use purpose and the like of the assist device by a system designer or the like.

As a target item, for example, there is an item relating to a result of rehabilitation performed by applying assist forces. More specifically, there are items relating to direct effects such as a walking speed, left-right symmetry, and a degree of enhancement of a continuous walking distance and items relating to indirect effects such as a degree of improvement of the amount of user's communication estimated from the amount of movement of a GPS terminal mounted on the user and the like as results of the rehabilitation.

Here, the "improvement effect data" represents data representing a correlation between an improvement effect that is a degree of improvement of a target item and an assist force. More specifically, the improvement effect data represents data representing a correlation between an improvement effect and details of assist forces (in other words, assist forces to be generated) applied to the user. For example, the improvement effect data is data representing a correlation between a height of the improvement rate of a user's athletic capability or a degree of a user's physical load or psychological load and magnitudes of torques of assist forces to be applied or the like.

Here, "details of assist forces" represents details that can be controlled by the control system for the assist forces to be generated. More specifically, for example, there are magnitudes of torques, input timings, torque patterns, a phase difference between left and right torque patterns, and the like relating to drive forces (and consequently, assist forces) that can be controlled by controlling the drive of the actuators as the details.

Here, "assist period" represents a period during which assist forces are generated for a user by the assist device. This assist period may be a continuous period or may be an intermittent period set at a predetermined interval. In this embodiment, a plurality of dates (for example, one month) is set as the assist period, and one day (precisely, a time at which rehabilitation is executed set for each day) is set as a reference unit period.

Figure 4:
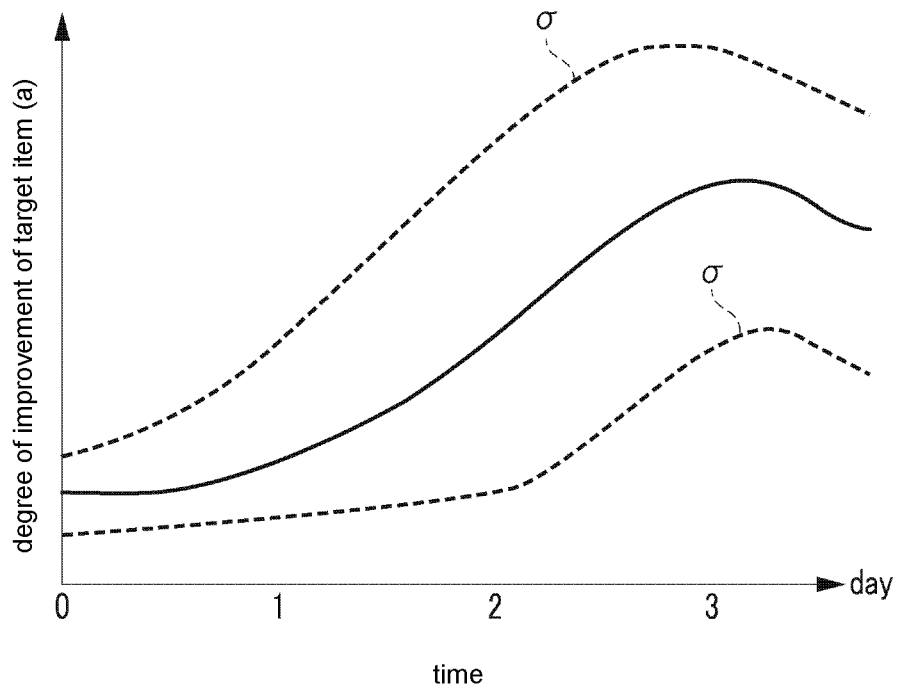
FIG. 4 represents graphs illustrating one example of improvement effect data stored by the control system illustrated in FIG. 1.

The improvement effect data, for example, as illustrated in FIG. 4, represents data representing a correlation between a degree of improvement of an improvement effect and a time when a predetermined assist force is generated. Such improvement effect data is stored in the improvement effect data storing unit 31 for each assist force that can be generated by the assist device 1.

The secondary effect data storing unit 32 stores secondary effect data for a plurality of types of secondary items for every reference unit period.

Here, "secondary items" are items corresponding to an effect on the user U as a result of an operation with which the assist device assists and represent items that are different from target items and are not set for the original purpose by the user U or the like. The secondary items are set in advance in accordance with the use purpose and the like of the assist device by a system designer or the like.

The secondary items include not only positive items such as muscle strength of another portion enhanced by predetermined rehabilitation together with muscle strength of a portion of which enhancement is to be achieved through the predetermined rehabilitation and the like, but also negative items such as fatigue occurring in accordance with the rehabilitation and a decrease in motivation for the rehabilitation.

Here, "secondary effect data" represents data representing a correlation between a secondary effect that is a degree of change in the secondary item and assist forces. More specifically, the secondary effect data represents data representing a correlation between a secondary effect and details of assist forces (in other words, assist forces to be generated) applied to the user.

In addition, here, "secondary effect data" represents data representing a correlation between a secondary effect that is a degree of change in the secondary item and assist forces. More specifically, the secondary effect data represents data representing a correlation between a degree of an effect on the user and details of assist forces applied to the user when the secondary effect occurs.

Figure 5:
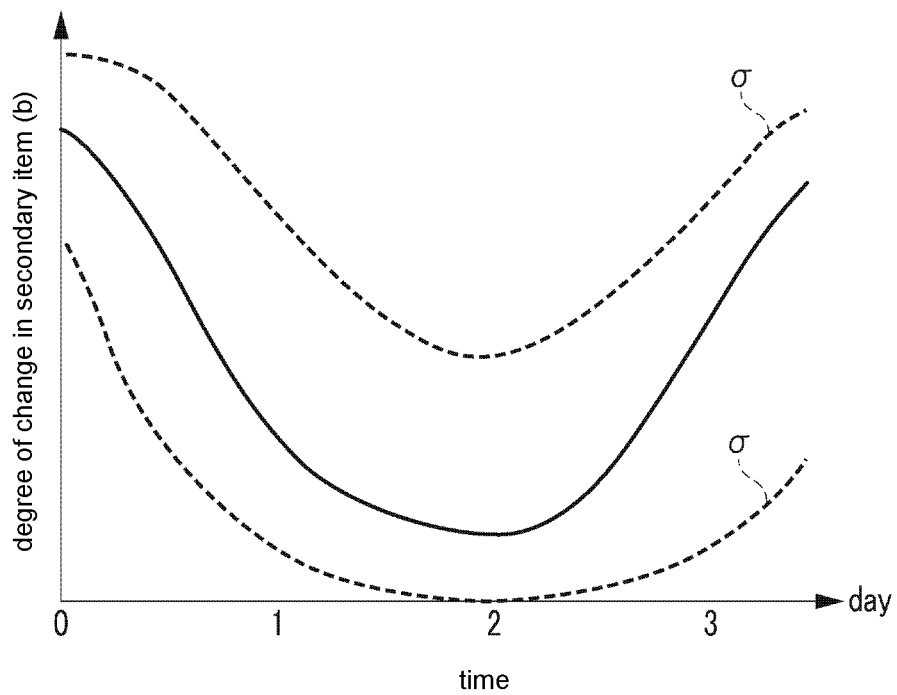
FIG. 5 represents graphs illustrating one example of secondary effect data stored by the control system illustrated in FIG. 1.

For example, as illustrated in FIG. 5, the secondary effect data is data representing a correlation between a degree of a secondary effect and a time when a predetermined assist force is applied. Such secondary effect data is stored in the secondary effect data storing unit 32 for each assist force that can be generated by the assist device 1.

Here, in this embodiment, for easy understanding, the assist device 1 can set an assist force in a stepped manner. For example, a torque of an assist force generated by the assist device 1 is selected from among three torques including a first torque T1, a second torque T2, and a third torque T3 and can be set through switching.

For this reason, in this embodiment, the improvement effect data and the secondary effect data are respectively stored in the improvement effect data storing unit 31 and the secondary effect data storing unit 32 for each of the three torques that can be generated.

The data recognizing unit 33 includes a data acquiring unit 33a that recognizes improvement effect data and secondary effect data and a ratio data calculating unit 33b that recognizes ratio data that is a ratio between a degree of the improvement effect and a degree of the secondary effect.

The data acquiring unit 33a recognizes improvement effect data from the improvement effect data storing unit 31 and recognizes secondary effect data from the secondary effect data storing unit 32 on the basis of the attributes of the user U recognized by the attribute recognizing unit 30.

The ratio data calculating unit 33b calculates ratio data for every reference unit period on the basis of the improvement effect data and the secondary effect data recognized by the data acquiring unit 33a.

Figure 6:
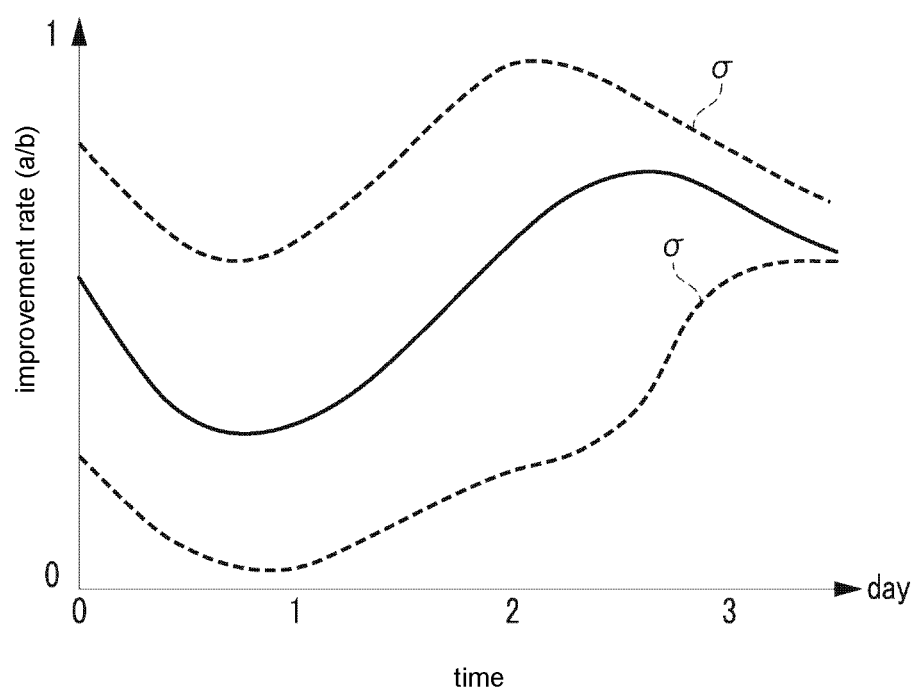
FIG. 6 represents graphs illustrating one example of ratio data calculated by the control system illustrated in FIG. 1.

For example, the ratio data is data, as illustrated in FIG. 6, representing a correlation between an improvement ratio, which is a ratio between a degree of the improvement effect and a degree of change in the secondary effect (in other words, a height of the improvement effect with respect to the secondary effect) when a predetermined assist force is applied, and a time. The ratio data calculating unit 33b calculates such ratio data for each assist force that can be generated by the assist device 1.

The schedule determining unit 34 includes an individual schedule determining unit 34a that determines an individual schedule and an entire schedule determining unit 34b that determines an entire schedule.

Here, "individual schedule" represents a schedule for an assist force to the generated for executing rehabilitation that is effective for the user U for each of target items in the entire assist period.

Here, "entire schedule" represents a schedule for an assist force to be generated for executing rehabilitation that is appropriate for the user in the entire assist period.

The individual schedule determining unit 34a determines an individual schedule for each target item on the basis of the ratio data calculated by the ratio data calculating unit 33b of the data recognizing unit 33.

The entire schedule determining unit 34b determines an entire schedule on the basis of the attributes of the user U recognized by the attribute recognizing unit 30 and the individual schedules determined by the individual schedule determining unit 34a and transmits the determined entire schedule to the tablet 2.

The configuration described with reference to FIG. 3 is one example of the assist device control system according to one or some exemplary embodiments of the disclosure. In other words, functions (processing units) realized by the hardware components or the program mounted on the server 3 according to this embodiment do not necessarily need to be realized by a single server.

For example, the functions may be realized using hardware components or a program mounted on a plurality of servers. In addition, for example, the function may be realized by the hardware components or the program mounted on the server in cooperation with the hardware components of the program mounted on at least one of the tablet and the assist device. Furthermore, for example, the functions may be realized by the hardware components or the program mounted on at least one of the tablet and the assist device without using the server.

Next, a process performed by the server 3 of the control system S when the assist device 1 determines a schedule for assist forces to be generated for the user U during a training period or an assist period will be described with reference to FIGS. 3 to 10. In addition, in this embodiment, for easy understanding, only a case in which a schedule for magnitudes of torques of assist forces is determined will be described.

Figure 7:
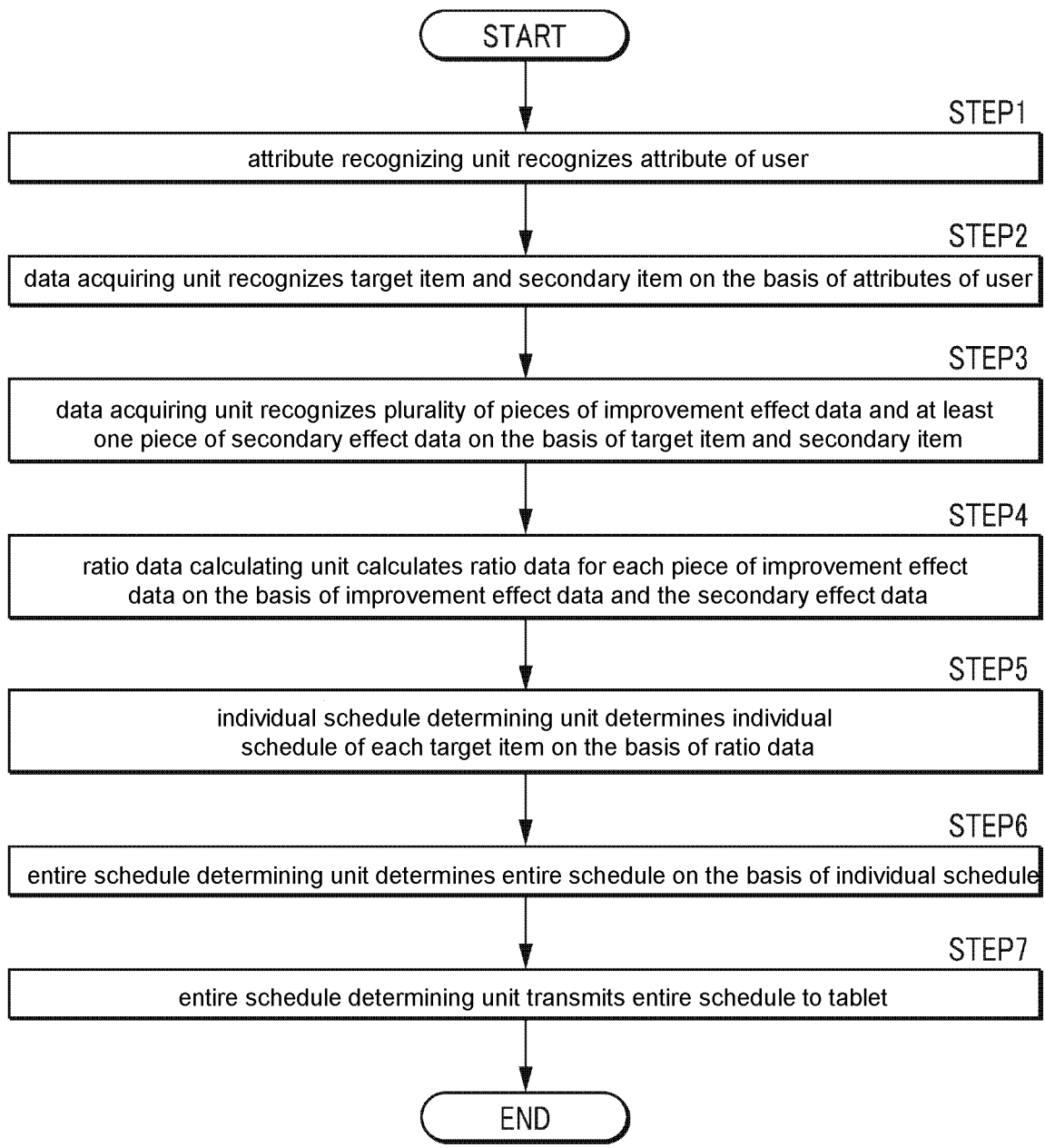
FIG. 7 is a flowchart illustrating a process executed when the control system illustrated in FIG. 1 determines an entire schedule.

In this process, first, the attribute recognizing unit 30 recognizes attributes of the user U on the basis of information input to the tablet 2 by the user U or the like (Step 1 in FIG. 7).

More specifically, the age of the user U, the purpose of rehabilitation of the user U (a disease or an injury that becomes a cause of the necessity for rehabilitation), scores relating to the current walking of the user U (for example, scores of items such as a walking speed, left-right symmetry, and the like) are recognized as attributes of the user U.

Next, the data acquiring unit 33a of the data recognizing unit 33 recognizes target items and secondary items on the basis of the recognized attributes of the user U (Step 2 in FIG. 7).

More specifically, the data acquiring unit 33a recognizes items of which enhancement is to be achieved as target items on the basis of the scores of the current walking of the user U. In this embodiment, it is assumed that a walking speed, left-right symmetry, and a continuous walking distance are recognized as the target items.

In addition, the data acquiring unit 33a recognizes items to be avoided or items that may be considered next time as secondary items on the basis of a physical strength estimated from the age of the user U and a disease or an injury that becomes a cause of the necessity for the rehabilitation of the user U. In this embodiment, it is assumed that the degree of accumulated fatigue is recognized as a secondary item.

Next, the data acquiring unit 33a recognizes improvement effect data for each target item that has been recognized from the improvement effect data storing unit 31 and recognizes secondary effect data for the secondary items from the secondary effect data storing unit 32 (Step 3 in FIG. 7).

Here, as illustrated in FIG. 4, the improvement effect data is data representing a correlation between a degree of improvement of the improvement effect and a time when a predetermined assist force is generated. The data acquiring unit 33a recognizes improvement effect data for each assist force that can be generated by the assist device 1. In this embodiment, improvement effect data is recognized for each of the first torque T1, the second torque T2, and the third torque T3 that can be selected.

In addition, as illustrated in FIG. 5, secondary effect data is data representing a correlation between a degree of the secondary effect and a time when a predetermined assist force is applied. The data acquiring unit 33a recognizes secondary effect data for each assist force that can be generated by the assist device 1. In this embodiment, similar to the improvement effect data, the secondary effect data is recognized for each of the first torque T1, the second torque T2, and the third torque T3 that can be selected.

Next, the ratio data calculating unit 33b of the data recognizing unit 33 calculates ratio data for each piece of the improvement effect data on the basis of the improvement effect data and the secondary effect data that have been recognized (Step 4 in FIG. 7).

More specifically, the ratio data calculating unit 33b, first, normalizes three target items on the basis of degrees of improvement of the target items. Thereafter, a value of each of the target items at each time point is divided by a value of the secondary item at each time point, whereby ratio data relating to each target item is calculated. In this way, the ratio data becomes data representing a correlation between an improvement rate that is a height of the improvement effect with respect to the secondary effect and a time.

Here, as described above, the data acquiring unit 33a recognizes improvement effect data and secondary effect data for each assist force that can be generated by the assist device 1. For this reason, in this process, the ratio data calculating unit 33b calculates ratio data as illustrated in FIG. 6 for each target item for each assist force that can be generated by the assist device 1.

Next, the individual schedule determining unit 34a of the schedule determining unit 34 determines an individual schedule of each target item on the basis of the calculated ratio data (Step 5 in FIG. 7).

Figure 8:
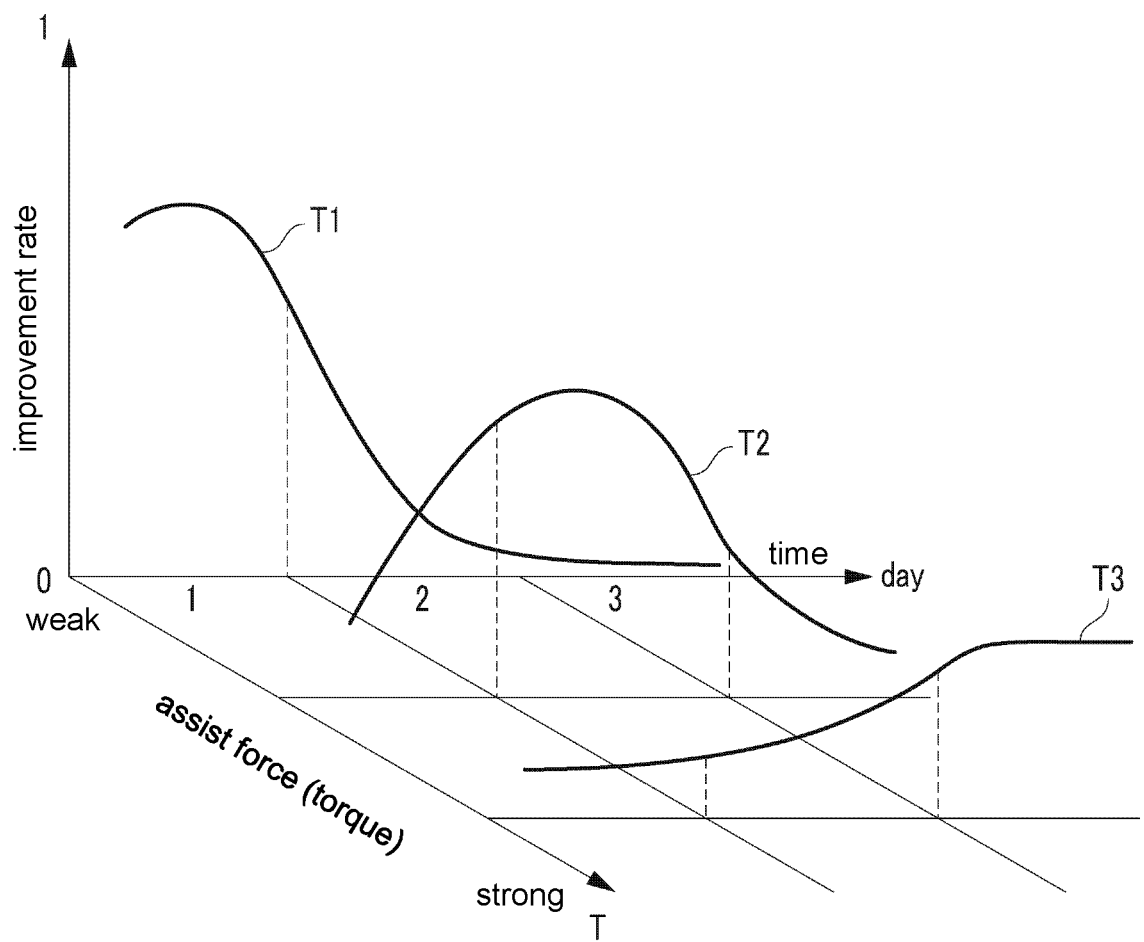
FIG. 8 represents graphs obtained by plotting the ratio data illustrated in FIG. 6 for each assist force to be generated.

More specifically, first, as illustrated in FIG. 8, the individual schedule determining unit 34a generates a map (a three-dimensional graph) having three elements of an improvement rate of a target item, a time (the number of days), and an assist force (the magnitude of the torque) as axes on the basis of the ratio data calculated for each assist force for each target item.

Figure 9:
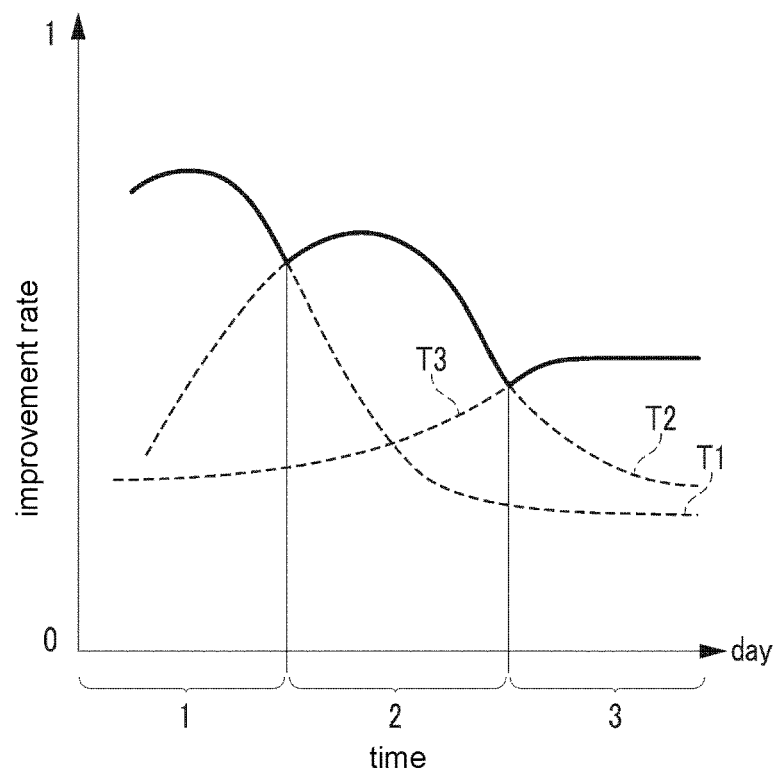
FIG. 9 is a graph illustrating one example of an individual schedule determined by the control system illustrated in FIG. 1.

Thereafter, the individual schedule determining unit 34a generates a two-dimensional graph having an improvement rate as its vertical axis and a time (the number of days) as its horizontal axis on the basis of the generated map as illustrated in FIG. 9. In this embodiment, the graph illustrated in FIG. 9 is a graph relating to an improvement rate having left-right symmetry.

In this embodiment, in this graph, a line (a line denoted by a broken line illustrated in FIG. 9) representing a relation between an improvement rate and a time is illustrated for each of the first torque T1, the second torque T2, and the third torque T3.

In addition, thereafter, the individual schedule determining unit 34a selects an assist force having a high improvement rate by comparing assist forces for each reference unit period (days) in the generated graph and determines an individual schedule.

In this embodiment, a schedule (a schedule based on a line denoted by a solid line in FIG. 9) in which the magnitude of the torque of the assist force to be generated is the first torque T1 on the first day, the second torque T2 on the second day, and the third torque T3 on the third day is determined as an individual schedule.

Here, in this embodiment, as a reference of an assist force employed when an individual schedule is determined (in other words, as an assist force to be prioritized), simply, a height of an improvement rate is employed. However, a reference for selecting an assist force employed when an individual schedule is selected in this embodiment is not limited thereto.

For example, a standard deviation of the improvement rate and a user's characteristic may be used as a reference. More specifically, it may be configured such that a user's characteristic is classified into a high-risk high-return type, an average type, and a low-risk low-return type, the size of an allowed range of a standard deviation is determined on the basis of the classification, assist forces of which standard deviations deviate from the allowed range are excluded, and then an assist force having a high improvement rate is employed. In addition, for example, an assist force may be selected from among assist forces of which improvement rates are equal to or higher than a predetermined rate.

Next, the entire schedule determining unit 34*b* of the schedule determining unit 34 determines an entire schedule on the basis of the determined individual schedules (Step 6 in FIG. 7).

Figure 10:
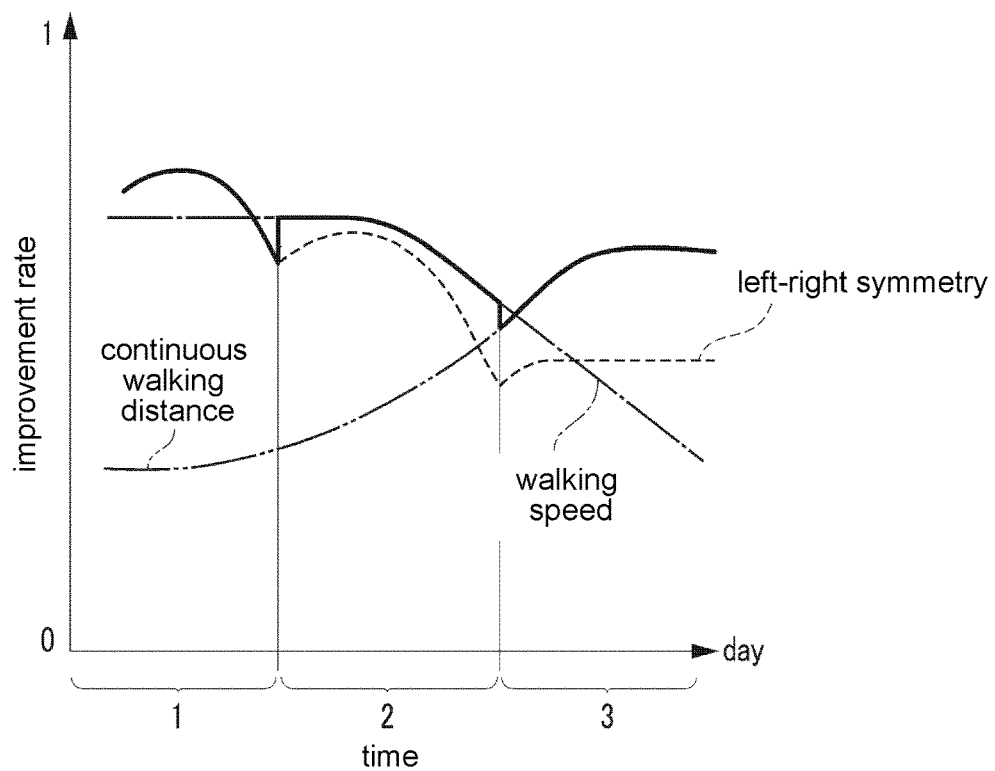
FIG. 10 is a graph illustrating one example of an entire schedule determined by the control system illustrated in FIG. 1.

More specifically, first, as illustrated in FIG. 10, the entire schedule determining unit 34*b* generates a two-dimensional graph having an improvement rate as its vertical axis and a time (the number of days) as its horizontal axis on the basis of the individual schedules for each target item determined by the individual schedule determining unit 34*a*.

In this embodiment, in this graph, a line representing a relation between an improvement rate and a time is represented for each of three target items (the walking speed, the left-right symmetry, and the continuous walking distance). In this embodiment, the left-right symmetry is denoted by a broken line, the walking speed is denoted by a one-dot chain line, and the continuous walking distance is denoted by a two-dot chain line.

Thereafter, the entire schedule determining unit 34*b* selects an assist force having a high improvement rate by comparing assist forces for every reference unit period (days) in the generated graph and determines an entire schedule.

In this embodiment, a schedule in which the magnitude of the torque of an assist force to be generated is set to a torque for the left-right symmetry on the first day, is set to a torque for the walking speed on the second day, and is set to a torque T3 for the continuous walking distance on the third day (a schedule based on a line denoted by a solid line in FIG. 10) is determined as an entire schedule.

Here, in this embodiment, as a reference for an assist force employed when an entire schedule is determined (in other words, as an assist force to be prioritized), simply, a height of the improvement rate is employed. However, a reference for selecting an assist force when an entire schedule is selected in this embodiment is not limited thereto.

For example, each target item is weighted in accordance with attributes of the user, and, in a case in which average values of improvement ratios of a plurality of target items are almost the same in the same reference unit period, an entire schedule may be determined by referring to an individual schedule for a target item of which weighting is high (a priority level is high) in the reference unit period.

Finally, the entire schedule determining unit 34*b* transmits the determined entire schedule to the tablet 2 (Step 7 in FIG. 7), and this process ends.

Thereafter, the entire schedule transmitted through the tablet 2 is presented to the user U and the like. Then, in a case in which the entire schedule is permitted by the user U or the like, the assist device 1 is controlled in accordance with the entire schedule.

In the control system S according to this embodiment, by performing processes similar to each other, an entire schedule relating to not only the magnitude of a torque relating to an assist force to be generated but also an output timing (a torque pattern) of the torque, the left-right balance of the torque (a ratio between the lengths of times in which legs are lifted), and a phase difference between left and right torques that are periodically generated is determined.

As described above, the control system S recognizes three target items and improvement effect data for such target items. Then, the control system S compares the improvement effect data relating to the three target items that have been recognized and determines a target item to be prioritized and an assist force to be generated for improving the target item for every reference unit period.

In this way, an assist force having a high improvement effect is determined as an assist force to be generated for every reference unit period set by delimiting the assist period. Therefore, according to the control system S, an assist force that is effective in the entire assist period can be generated.

As above, although the embodiment illustrated in the drawing has been described, the disclosure is not limited to such a form.

For example, in the embodiment described above, three items including the walking speed, the left-right symmetry, and the continuous walking distance are recognized as target items, and a degree of accumulated fatigue is recognized as a secondary item. However, the assist device control system according to one or some exemplary embodiments of the disclosure is not limited to such a configuration and may recognize a plurality of target items and recognize at least one secondary item. For example, two or four or more target items may be recognized, and two or more secondary items may be recognized.

In addition, in the embodiment described above, not only the target items but also the secondary items are recognized, and individual schedules and an entire schedule are determined using ratio data calculated on the basis of the improvement effect data and the secondary effect data. The reason for this is that an improvement effect in the entire assist period may consequently decrease when an assist force having a high improvement effect and a high secondary effect is generated. However, the assist device control system according to one or some exemplary embodiments of the disclosure is not limited to such a configuration and may not refer to a secondary item.

In addition, in the embodiment described above, target items and secondary items are recognized in accordance with the attributes of the user U. The reason for this is that, when target items and secondary items and improvement effect data and secondary effect data thereof are recognized in accordance with the attributes of a user in this way, an assist force determined to be generated in accordance therewith can efficiently enhance items that are appropriate for user's requests and situations.

However, the assist device control system according to one or some exemplary embodiments of the disclosure is not limited to such a configuration and may recognize target items and secondary items regardless of the attributes of a user.

For example, either target items or secondary items may be recognized in accordance with the attributes of a user. In addition, for example, target items or secondary items may be directly designated by a user or the like without referring to the attributes of the user. Furthermore, for example, a population of target items and secondary items that can be selected is generated in accordance with the attributes of a user, and the user or the like may be allowed to select target items and secondary items from the population.

For example, in the embodiment described above, an entire schedule is determined by determining an assist force to be generated for every unit period (one day). However, depending on an item that is a target to be improved, the most efficient schedule may not be necessarily determined by delimiting the period in units of one day.

For example, in the entire schedule illustrated in FIG. 10 in the embodiment described above, it can be regarded to be preferable to generate an assist force for improving a walking speed than an assist force for improving the left-right symmetry in a time frame of a final stage of the first day.

Thus, it is possible to configure the schedule determining unit to compare recognized improvement effect data, determine a generation unit period by adjusting each reference unit period, determine a target item to be prioritized among the target items recognized for every generation unit period, and determine an assist force to be generated for every generation unit period on the basis of improvement effect data corresponding to the determined target item to be prioritized.

Figure 11:
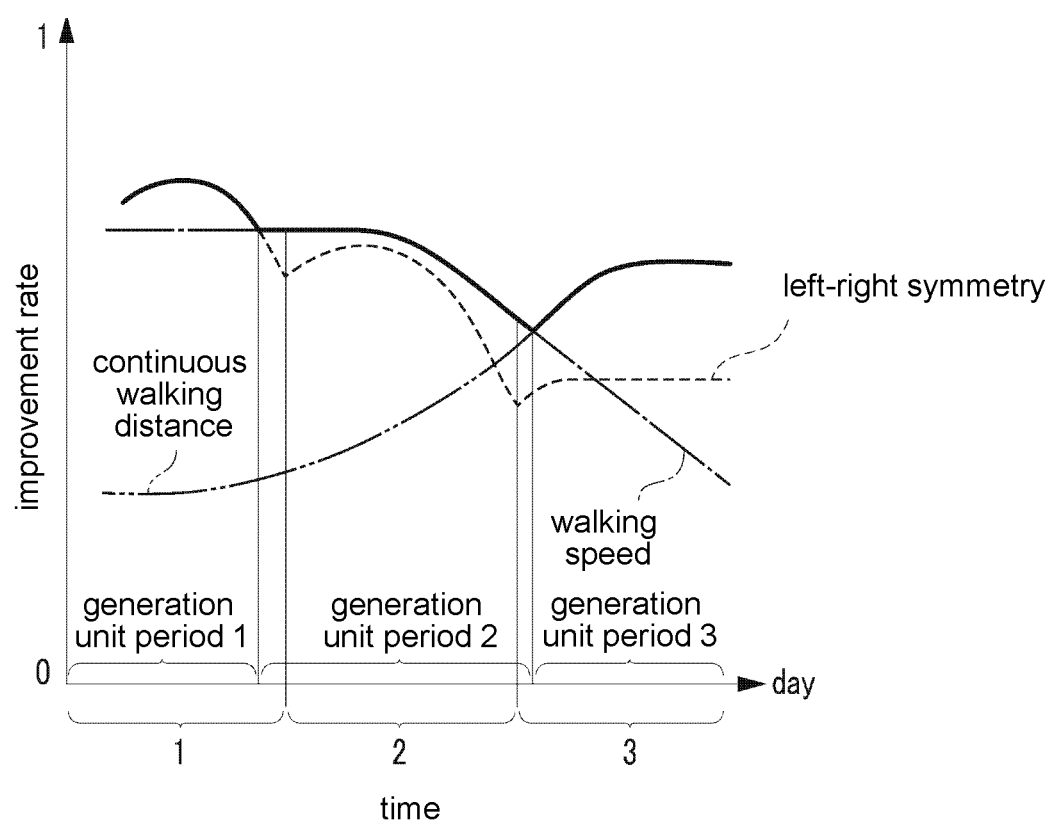
FIG. 11 is a graph illustrating one example of an entire schedule determined by a control system according to a modified example.

More specifically, as illustrated in FIG. 11, an assist force having the best efficiency (in other words, a high improvement rate) at a time without being limited to the reference unit period among assist forces relating to the left-right symmetry, the walking speed, and the continuous walking distance is employed as an assist force to be generated with priority. Then, a timing at which the assist force is changed is set as a delimiter of the generation unit period.

In this example, a timing at which the generation of an assist force relating to the walking speed is switched to be prioritized with respect to the generation of an assist force relating to the left-right symmetry is set to be earlier than a boundary between the first day and the second day, and a timing at which the generation of an assist force relating to the continuous walking distance is switched to be prioritized with respect to the generation of an assist force relating to the walking speed is set to be later than a boundary between the second day and the third day.

As a result, a generation unit period 1 at which an assist force relating to the left-right symmetry is generated and a generation unit period 3 at which an assist force relating to the continuous walking distance is generated are shorter than the original reference unit period (one day). On the other hand, a generation unit period 2 at which an assist force relating to the walking speed is generated is longer than the original reference unit period.

In this way, in this entire schedule, a timing at which switching between assist forces to be generated is performed is delimited by a generation unit period that is more appropriate than the reference unit period such that generation of an assist force having the highest efficiency can be continued without being limited to the reference unit period. In other words, a timing at which switching between assist forces to be generated is performed becomes more appropriate.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. An assist device control system controlling an assist device that generates an assist force corresponding to an operation of a user during a predetermined assist period, the assist device control system comprising:
   an improvement effect data storing unit that stores improvement effect data, which represents a correlation between an improvement effect that is an effect on the user according to the assist force and the assist force, for each target item for every reference unit period set by delimiting the assist period for a plurality of types of target items;
   a data recognizing unit that recognizes a plurality of the target items and recognizes the improvement effect data for each of the target items; and
   a schedule determining unit that compares the improvement effect data being recognized, determines a target item to be prioritized from among the target items being recognized for every reference unit period, and determines the assist force to be generated for every reference unit period on a basis of the improvement effect data corresponding to the determined target item to be prioritized.

2. The assist device control system according to claim 1, further comprising a secondary effect data storing unit that stores secondary effect data, which represents a correlation between a secondary effect that is an effect different from the improvement effect applied to the user in accordance with the assist force and the assist force for each secondary item that is an item different from the target items, for a plurality of types of secondary items for every reference unit period,
   wherein the data recognizing unit recognizes the plurality of target items and recognizes at least one of the secondary items, recognizes the improvement effect data for each of the target items being recognized and the secondary effect data for the secondary items being recognized, and recognizes ratio data that is a ratio between a degree of the improvement effect and a degree of the secondary effect on a basis of each piece of the improvement effect data and the secondary effect data that have been recognized, and
   wherein the schedule determining unit compares the ratio data being recognized and determines a target item to be prioritized from among the recognized target items for every reference unit period.

3. The assist device control system according to claim 1, wherein the data recognizing unit recognizes the target items on a basis of attributes of the user.

4. The assist device control system according to claim 2, wherein the data recognizing unit recognizes the target items on a basis of attributes of the user.

5. The assist device control system according to claim 1, wherein the schedule determining unit compares the improvement effect data being recognized and determines a generation unit period by adjusting each reference unit period, determines the target item to be prioritized from among the target items being recognized for every generation unit period, and determines the assist force to be generated for every generation unit period on a basis of the improvement effect data corresponding to the determined target item to be prioritized.

6. The assist device control system according to claim 2, wherein the schedule determining unit compares the improvement effect data being recognized and determines a generation unit period by adjusting each reference unit period, determines the target item to be prioritized from among the target items being recognized for every generation unit period, and determines the assist force to be generated for every generation unit period on a basis of the improvement effect data corresponding to the determined target item to be prioritized.

7. The assist device control system according to claim 3, wherein the schedule determining unit compares the improvement effect data being recognized and determines a generation unit period by adjusting each reference unit period, determines the target item to be prioritized from among the target items being recognized for every generation unit period, and determines the assist force to be generated for every generation unit period on a basis of the improvement effect data corresponding to the determined target item to be prioritized.

8. The assist device control system according to claim 4, wherein the schedule determining unit compares the improvement effect data being recognized and determines a generation unit period by adjusting each reference unit period, determines the target item to be prioritized from among the target items being recognized for every generation unit period, and determines the assist force to be generated for every generation unit period on a basis of the improvement effect data corresponding to the determined target item to be prioritized.

* * * * *